(12) United States Patent
Meister et al.

(10) Patent No.: US 9,775,997 B2
(45) Date of Patent: Oct. 3, 2017

(54) NEURAL CODING WITH SHORT INTER PULSE INTERVALS

(71) Applicant: MED-EL Elektromedizinische Geraete GmbH, Innsbruck (AT)

(72) Inventors: Dirk Meister, Innsbruck (AT); Peter Schleich, Telfs (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 143 days.

(21) Appl. No.: 14/875,775

(22) Filed: Oct. 6, 2015

(65) Prior Publication Data

US 2016/0101285 A1 Apr. 14, 2016

Related U.S. Application Data

(60) Provisional application No. 62/061,191, filed on Oct. 8, 2014.

(51) Int. Cl.
*A61N 1/00* (2006.01)
*A61N 1/36* (2006.01)
*A61N 1/05* (2006.01)

(52) U.S. Cl.
CPC ........ *A61N 1/36032* (2013.01); *A61N 1/0541* (2013.01)

(58) Field of Classification Search
CPC .......................... A61N 1/36032; A61N 1/0541
USPC .......................................................... 607/57
See application file for complete search history.

(56) References Cited

U.S. PATENT DOCUMENTS

| | | |
|---|---|---|
| 6,594,525 B1 | 7/2003 | Zierhofer |
| 7,920,923 B2 | 4/2011 | Laback et al. |
| 2004/0172101 A1 | 9/2004 | Van Hoesel |
| 2010/0249880 A1 | 9/2010 | Aschbacher et al. |
| 2011/0004274 A1 | 1/2011 | Schleich et al. |

(Continued)

OTHER PUBLICATIONS

International Searching Authority, Authorized Officer Blaine R. Copenheaver, International Search Report and Written Opinion, PCT/US2015/054121, dated Dec. 28, 2015, 12 pages.

(Continued)

*Primary Examiner* — Amanda Patton
*Assistant Examiner* — Philip C Edwards
(74) *Attorney, Agent, or Firm* — Sunstein Kann Murphy & Timbers LLP

(57) ABSTRACT

Arrangements are described for generating electrode stimulation signals for an implanted electrode array having multiple stimulation contacts. An audio input preprocessor receives an input audio signal and generates band pass signals that represent associated bands of audio frequencies. A band pass signal analyzer analyzes each band pass signal to detect when one of the band pass signal components reaches a defined transition event state. A stimulation signal generator generates a set of electrode stimulation signals for the stimulation contacts from the band pass signals such that the electrode stimulation signals to a given stimulation contact: i. use a transition event stimulation pattern whenever a transition event is detected in a band pass signal associated with the given stimulation contact, and ii. use a different non-transition stimulation pattern after the transition event stimulation pattern until a next subsequent transition event is detected.

21 Claims, 7 Drawing Sheets

(56) References Cited

U.S. PATENT DOCUMENTS

2012/0004706 A1* 1/2012 Meister .............. A61N 1/36032
607/57
2014/0058478 A1 2/2014 Fruhauf et al.

OTHER PUBLICATIONS

Hancock, et al, "Neural ITD coding with bilateral cochlear implants: effect of binaurally coherent jitter", *J. Neurophysiol* 108, Aug. 1, 2012, pp. 714-728, 15 pages.

* cited by examiner

NEURAL CODING WITH SHORT INTER PULSE INTERVALS

This application claims priority from U.S. Provisional Patent Application 62/061,191, filed Oct. 8, 2014, which is incorporated herein by reference in its entirety.

FIELD OF THE INVENTION

The present invention relates to auditory implant systems, and more specifically to electric stimulation arrangements in cochlear implant systems and other implantable auditory prostheses.

BACKGROUND ART

A normal human ear transmits sounds as shown in FIG. 1 through the outer ear 101 to the tympanic membrane 102 which moves the bones of the middle ear 103 that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted electrode can electrically stimulate auditory nerve tissue with small currents delivered by multiple electrode contacts distributed along the electrode. Although the following discussion is specific to cochlear implants, some hearing impaired persons are better served when the stimulation electrode is implanted in other anatomical structures. Thus auditory implant systems include brainstem implants, middle brain implants, etc. each stimulating a specific auditory target in the hearing system.

FIG. 1 also shows some components of a typical cochlear implant system where an external microphone provides an audio signal input to an external implant processor 111 in which various signal processing schemes can be implemented. For example, signal processing approaches that are well-known in the field of cochlear implants include continuous interleaved sampling (CIS) digital signal processing, channel specific sampling sequences (CSSS) digital signal processing (as described in U.S. Pat. No. 6,348,070, incorporated herein by reference), spectral peak (SPEAK) digital signal processing, fine structure processing (FSP) and compressed analog (CA) signal processing.

The processed signal is then converted into a digital data format for transmission by external transmitter coil 107 into the implant stimulator 108. Besides receiving the processed audio information, the implant stimulator 108 also performs additional signal processing such as error correction, pulse formation, etc., and produces a stimulation pattern (based on the extracted audio information) that is sent through an electrode lead 109 to an implanted electrode array 110. Typically, this electrode array 110 includes multiple electrode contacts 112 on its surface that provide selective stimulation of the cochlea 104.

FIG. 2 shows various functional blocks in a typical CI signal processing system using the CIS stimulation strategy. An audio input pre-processor 201 includes a pre-emphasis filter 203 that receives an input audio signal from a microphone and attenuates strong frequency components in the audio signal below about 1.2 kHz. FIG. 3 shows a typical example of a short time period of an input audio signal from a microphone. The sound pre-processor 201 also includes multiple band pass filters (BPFs) 204 that decompose the audio signal from the pre-emphasis filter 203 into multiple spectral band pass signals as shown, for example, in FIG. 4. As shown in FIG. 5, each band pass signal 501 is thought of as having a fine structure component 502 and an envelope component 503 (typically derived by Hilbert transformation). The filtered envelope signal 504 oscillates around the zero reference axis line with a frequency that is related to the fundamental frequency F0 of the band pass filter.

A sound processor 202 includes envelope detectors 205 that extract the slowly-varying band pass envelope components of the band pass signals, for example, by full-wave rectification and low pass filtering. The sound processor 202 also includes a non-linear (e.g., logarithmic) mapping module 206 that performs compression of the envelopes to fit the patient's perceptual characteristics, and the compressed envelope signals are then multiplied with carrier waveforms by modulators 207 to produce electrode stimulation signals in the specific form of non-overlapping biphasic output pulses for each of the stimulation contacts (EL-1 to EL-n) in the electrode array that is implanted in the cochlea 104 reflecting the tonotopic neural response of the cochlea.

CIS stimulation imposes a fixed stimulation rate on the electrical pulses that form the electrode stimulation signals and therefore cannot represent periodicity components of the input audio signal. On the other hand, FSP stimulation (and its variants) does represent the inherent periodicity of sensed audio signals. FSP generates electrode stimulation signals using patterns of stimulation pulse trains responsive to detection of specific pre-defined band pass components such as zero crossing events. In FSP, CSSS sequences are applied at zero crossings of the fine structure components. The CSSS sequences can transmit information on instantaneous frequency up to patient-specific limits.

U.S. Pat. No. 7,920,923 to Laback describes adding phase jitter to the stimulation signal pulses to improve perception of interaural time difference (ITD) information. Binaural audio signals are generated that represent sound associated with a user's left and right ears respectively. Based on the binaural audio signals, corresponding binaural stimulation signals are generated for electrical stimulation of auditory nerve tissue of the user, where the binaural stimulation signals include fine structure components with periodic characteristics and ITD information. A phase jitter component is added to the binaural stimulation signals to reduce the periodic characteristics of the fine structure component while preserving the ITD information between the left and right ears. Since binaural adaptation is a phenomenon which occurs for periodic signals, introducing artificial phase jitter into the stimulation signals reduces the periodicities of the signals to make the listener less prone to binaural adaptation. The artificial phase jitter is based on the fine structure component.

While Laback showed that adding phase jitter improves hearing directionality, Hancock et al., *Neural ITD Coding with Bilateral Cochlear Implants: Effect of Binaurally Coherent Jitter*, J Neurophysiol., 108(3), 2012 Aug. 1, p. 714-728 (incorporated herein by reference) found that this improvement is mainly due to the use of short inter-pulse intervals. When auditory neurons are electrically stimulated, their responses are in phase with the electrical stimuli up to a patient-specific stimulation rate. Hancock reported that the neural response to constant-rate pulse trains in the inferior colliculus of cats is an on-going response that is phase-locked to stimuli of up to 320 pps. Above the 320 pps stimulation rate limit, the auditory neurons fire only in response to the onset of pulse bursts. Hancock further showed that introducing short inter-pulse intervals with random phase-jitter significantly changed the neural response in the inferior colliculus for stimulation rates above 320 pps in sustaining the firing a significant number of neurons. But introducing random phase jitter may have detrimental effects on other auditory functions, for example rate pitch perception, and speech understanding potentially may suffer. And current auditory implant systems have no way to extend the range of phase-locking of neural responses to stimulation pulses.

SUMMARY OF THE INVENTION

Embodiments of the present invention are directed to auditory implant system arrangements for generating electrode stimulation signals for an implanted electrode array having multiple stimulation contacts. An audio input pre-processor receives an input audio signal and generates band pass signals that represent associated bands of audio frequencies. A band pass signal analyzer analyzes each band pass signal to detect when one of the band pass signal components reaches a defined transition event state. A stimulation signal generator generates a set of electrode stimulation signals for the stimulation contacts from the band pass signals such that the electrode stimulation signals to a given stimulation contact: i. use a transition event stimulation pattern whenever a transition event is detected in a band pass signal associated with the given stimulation contact, and ii. use a different non-transition stimulation pattern after the transition event stimulation pattern until a next subsequent transition event is detected.

The transition event stimulation pattern may form at least one pair of sequential biphasic pulses with short inter-pulse-interval, and/or the non-transition stimulation pattern may form a single biphasic pulse. The transition event may be onset of a voiced pitch period, a zero crossing of a band pass fine structure immediately following the zero crossing of a filtered band pass envelope, the occurrence of a given multiple number of zero crossings in the band pass fine structure, and/or a zero crossing of a filtered band pass envelope.

DETAILED DESCRIPTION OF SPECIFIC EMBODIMENTS

Embodiments of the present invention improve ITD perception in auditory implant patients while improving or at least maintaining speech perception. This improves hearing directionality, sound source locating, and speech understanding in noisy conditions.

Figure 6:
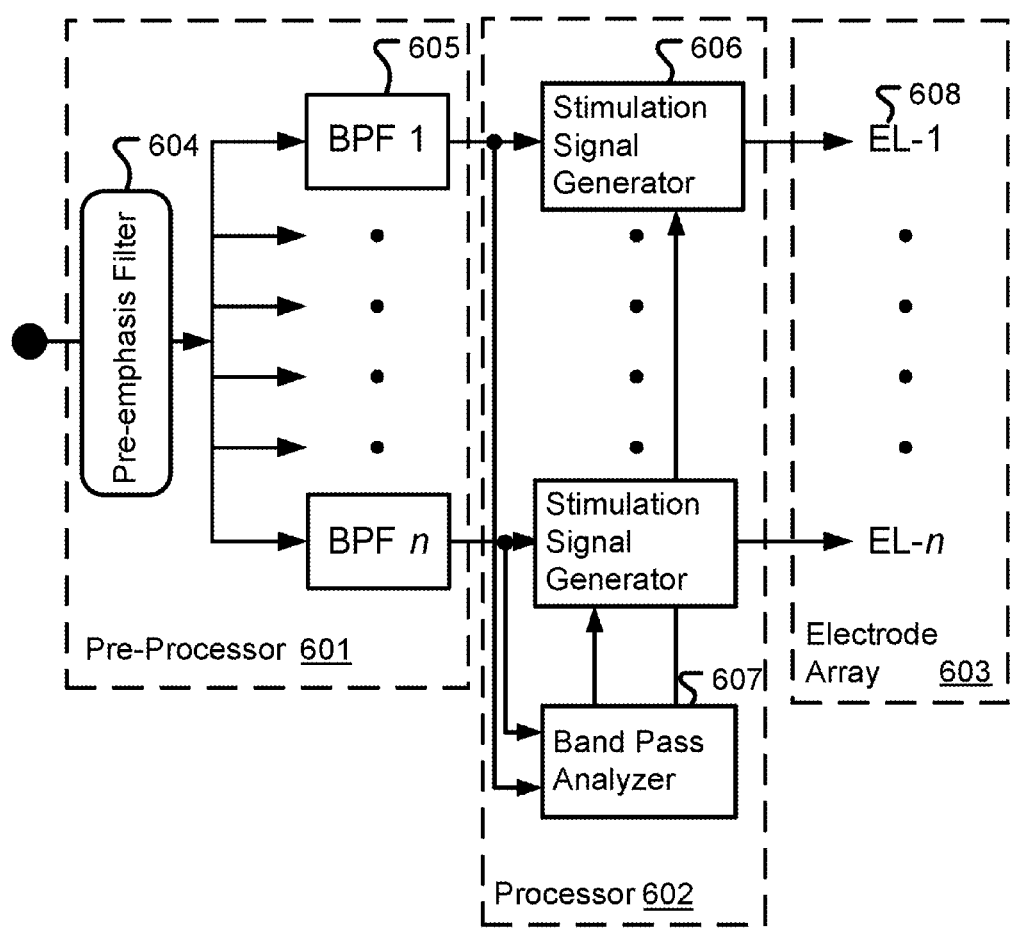
FIG. 6 shows an example of a signal processing arrangement according to one specific embodiment of the present invention.

FIG. 6 shows one such embodiment of a signal processing arrangement in an auditory implant system that generates electrode stimulation signals for the stimulation contacts in an implanted electrode array such as a cochlear implant electrode array. An audio input preprocessor 601 receives an input audio signal, passes it through a pre-emphasis filter 604 and then through multiple parallel band pass filters (BPFs) 605 that decompose the input audio signal into multiple band pass signals that represent associated bands of audio frequencies. Processor 602 includes a band pass signal analyzer 607 that analyzes each of the BPF band pass signals to detect when one of the band pass signal components reaches a defined transition event state. A stimulation signal generator 606 also receives the band pass signals and generates a set of corresponding electrode stimulation signals for the stimulation contacts 608.

Specifically, the band pass signal analyzer 607 provides an input to control each band pass channel stimulation signal generator 606 to produce stimulation signals using a given transition event stimulation pattern whenever the band pass signal analyzer 607 detects a transition event in a band pass signal associated with the given stimulation contact 608. After the transition event stimulation pattern, the band pass channel stimulation signal generator 606 then producing stimulation signals using a different non-transition stimulation pattern until the band pass signal analyzer 607 detects a next subsequent transition event.

Figure 7:
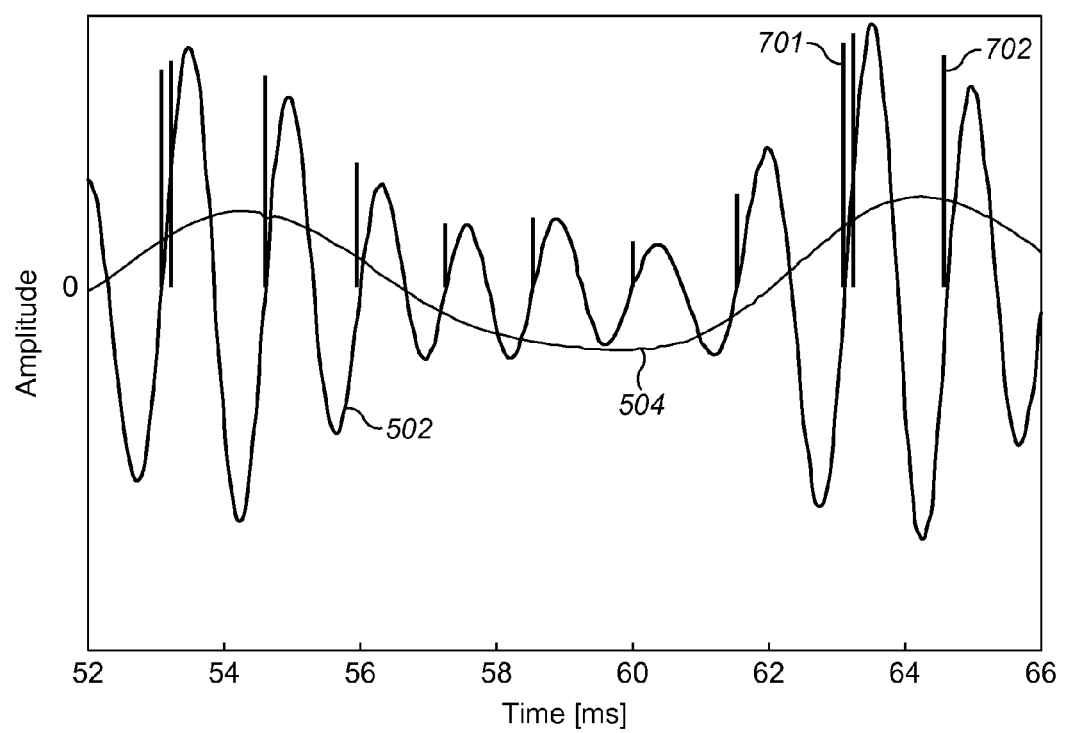
FIG. 7 shows an example of band pass signal components and different stimulation patterns according to an embodiment of the present invention.

FIG. 7 shows an example of band pass signal components and different stimulation patterns according to an embodiment of the present invention. In the example shown in FIG. 7, the transition event stimulation pattern 701 is a CSSS sequence comprising a pair of sequential biphasic pulses, while the non-transition stimulation pattern 702 is a different CSSS sequence comprising a single biphasic pulse (NB: for diagram clarity, only the amplitude of the first phase of the biphasic pulses is shown in FIG. 7).

In the specific example shown in FIG. 7, the specific transition event that triggers a transition event stimulation pattern 701 is the first negative-to-positive zero crossing in the band pass fine structure component 502 that occurs after a negative-to-positive zero crossing of the filtered DC-free band pass envelope component 504 at the onset of a voiced pitch period. In the stimulation signal pulse sequence immediately following each zero crossing of the filtered DC-free band pass envelope 504 (or derivative of the band pass envelope), a transition event stimulation pattern 701 that adds an extra stimulation pulse with a short inter-pulse interval to the preceding stimulation pulse can provide improved ITD perception while improving or transition event stimulation pattern 701 speech perception. Typically the inter-pulse interval in the transition event stimulation pattern 701 will be shorter than the refractory period of the stimulated neurons. For example, inter-pulse intervals ≤400 µs, or ≤250 µs have been found suitable.

Figure 8:
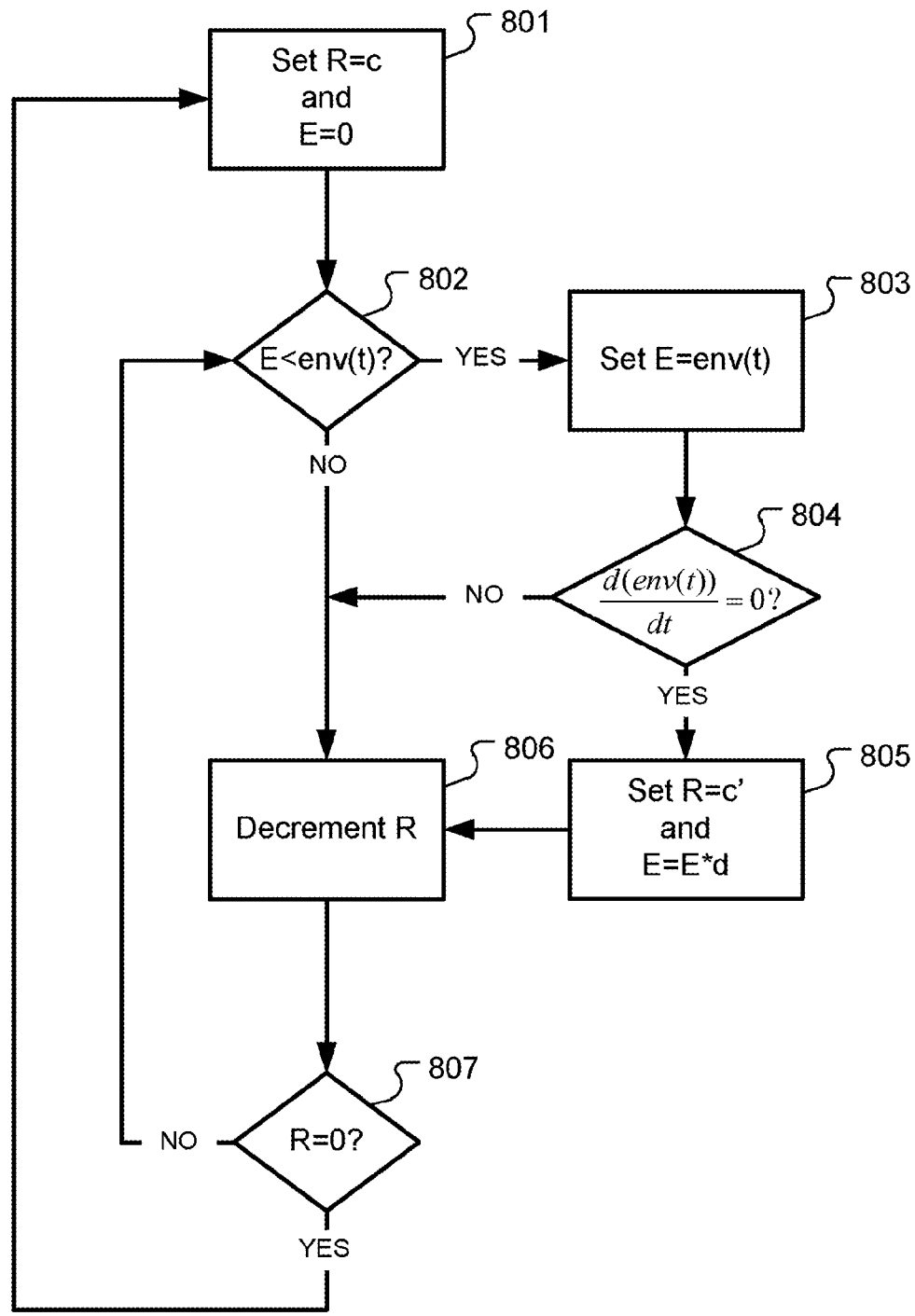
FIG. 8 shows an example of an onset of a voiced pitch period transition event detection method according to an embodiment of the present invention.

In the specific example shown in FIG. 8, the specific transition event that triggers a transition event stimulation pattern 701 is determined so as to occur preferentially at the onset of a voiced pitch period, i.e. at the onset of a vowel. First in step 801, a counter R is set to a specific pre-defined value c and the envelope magnitude E is reset to zero. The value c may be chosen to reflect the voiced syllable period of the input audio signal. In step 802, for each time instant t, the stored envelope magnitude E is compared to the current envelope signal env(t) and set to env(t) when E is smaller, step 803, and otherwise E remains unchanged. Expressed in mathematical terms, that is E=max(E, env(t)). Second, for the case where the stored envelope magnitude E has been updated in step 803, the derivative of the current envelope is checked, step 804, to determine a local maximum of the envelope signal. This is the case when the derivative of the envelope changes sign or is close to or equals zero. In this case, a transition event at the onset of a voiced pitch period is detected in step 804, and a transition event stimulation pattern 701 may be triggered. In addition, the counter R is set to a new specific pre-defined value c' and the envelope magnitude E may be multiplied with a pre-defined value d, step 805. The value d may be chosen so as to fulfill the trigger condition only when the envelope exceeds the stored envelope magnitude E by some given amount, thereby emphasizing trigger events at the onset. The value c' may be identical to c. Then the counter R is decremented, step 806, and upon reaching zero in step 807, continues with step 801, otherwise with step 802.

Figure 1:
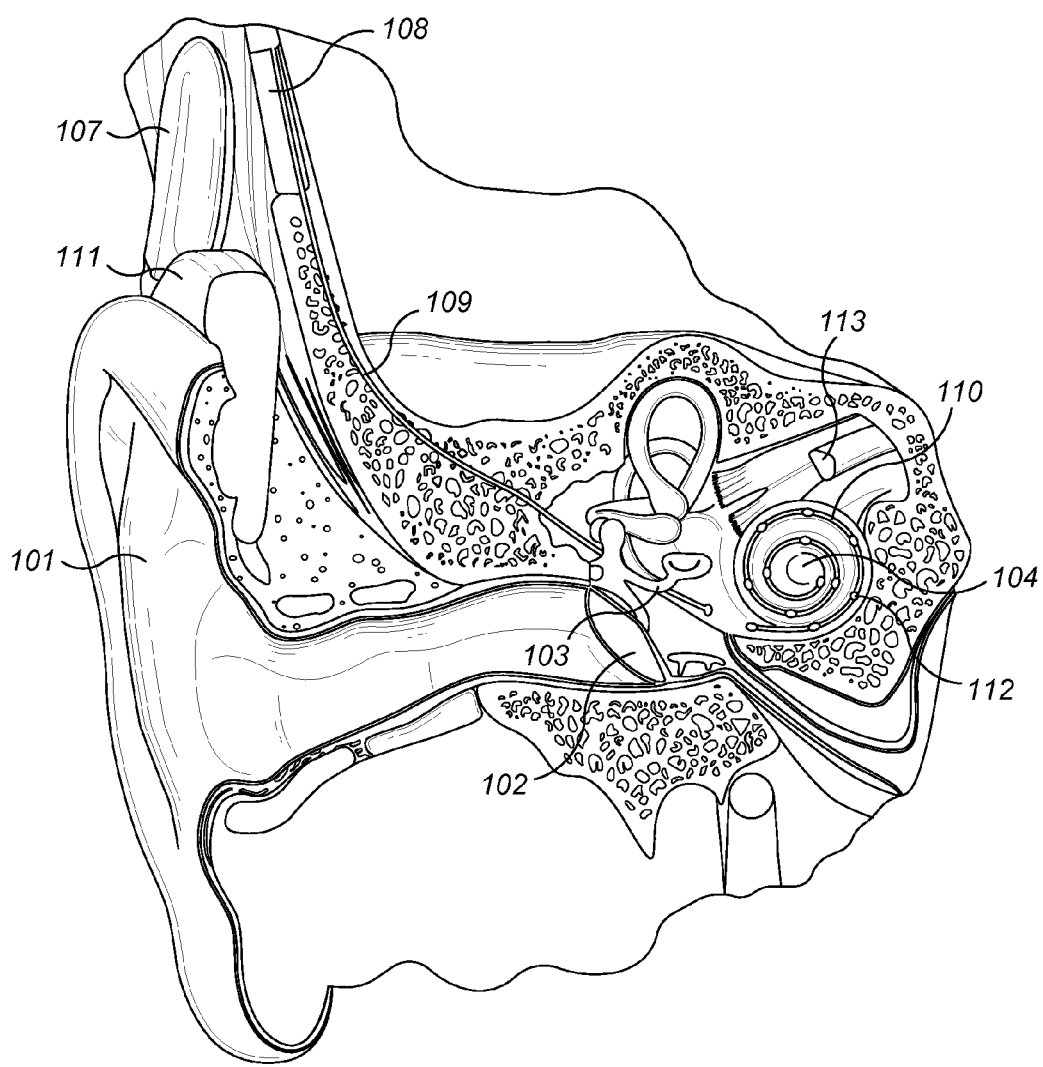
FIG. 1 shows a section view of a human ear with a typical auditory prosthesis system designed to deliver electric stimuli to the inner ear and acoustic stimuli at the ear canal.
Figure 2:
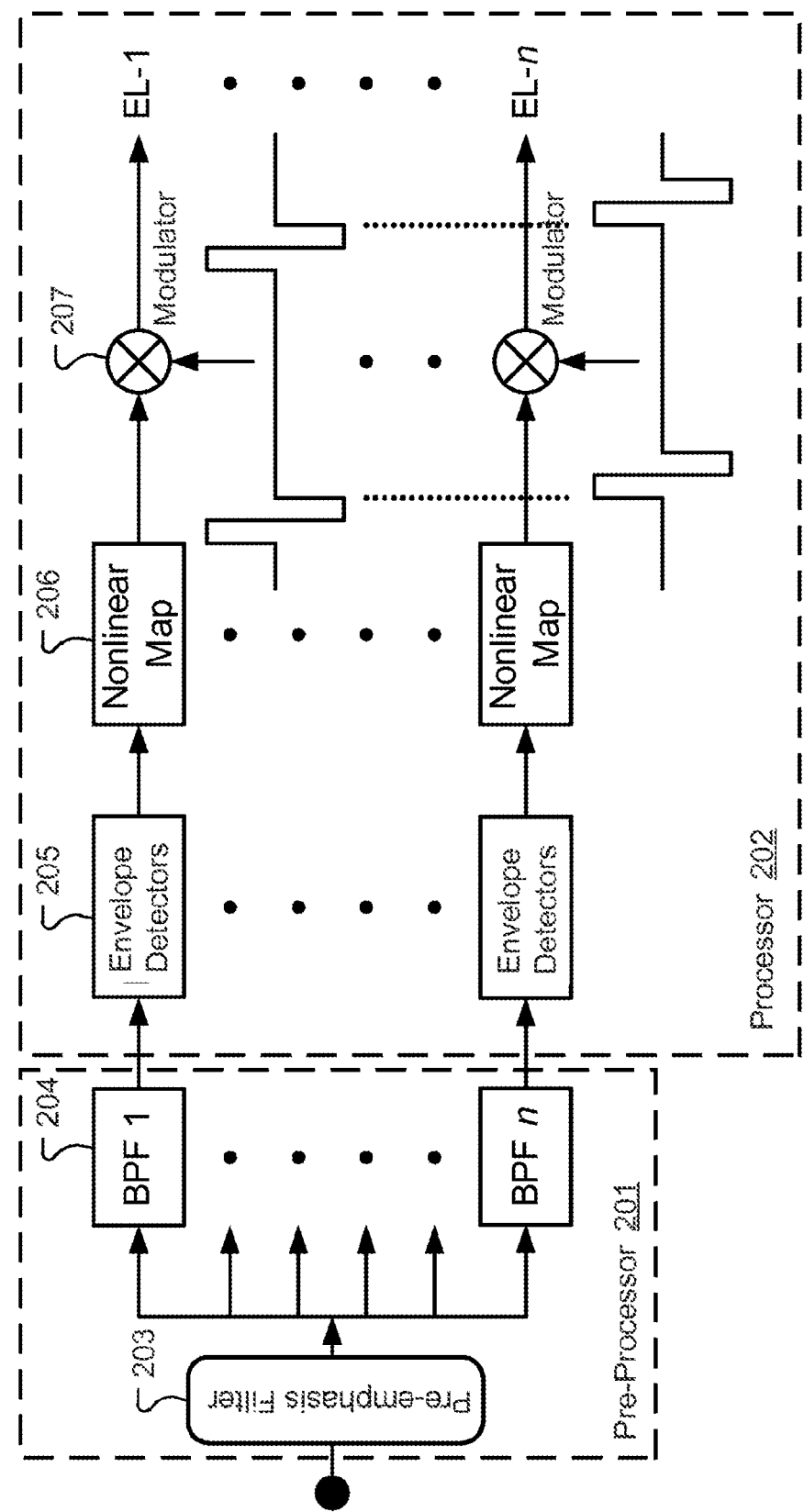
FIG. 2 shows various functional blocks in a continuous interleaved sampling (CIS) processing system.
Figure 3:
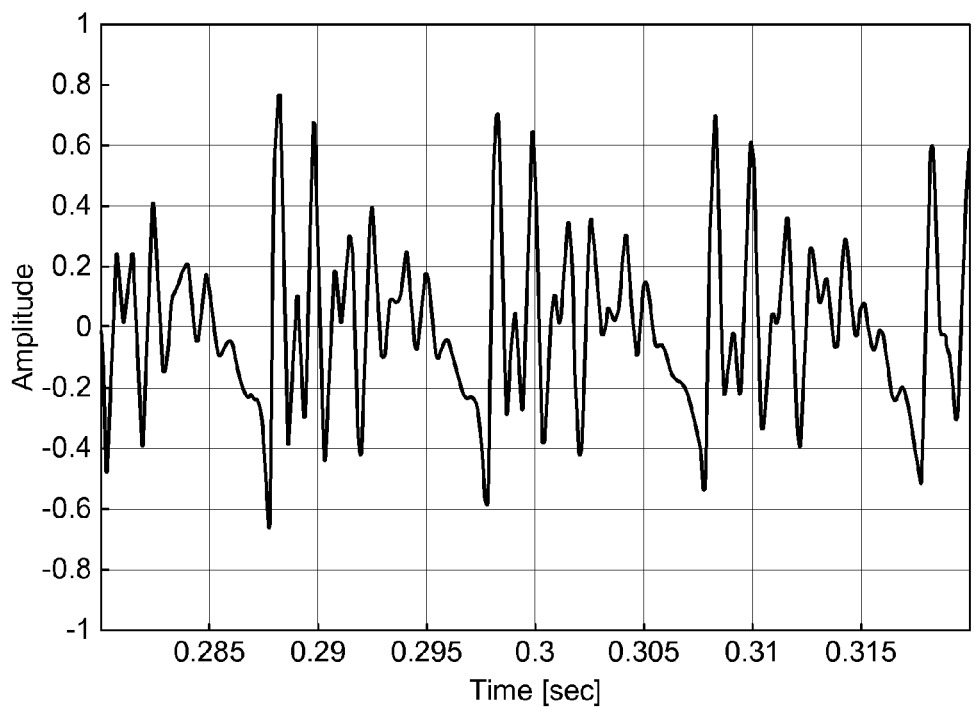
FIG. 3 shows an example of a short time period of an audio speech signal from a microphone.
Figure 4:
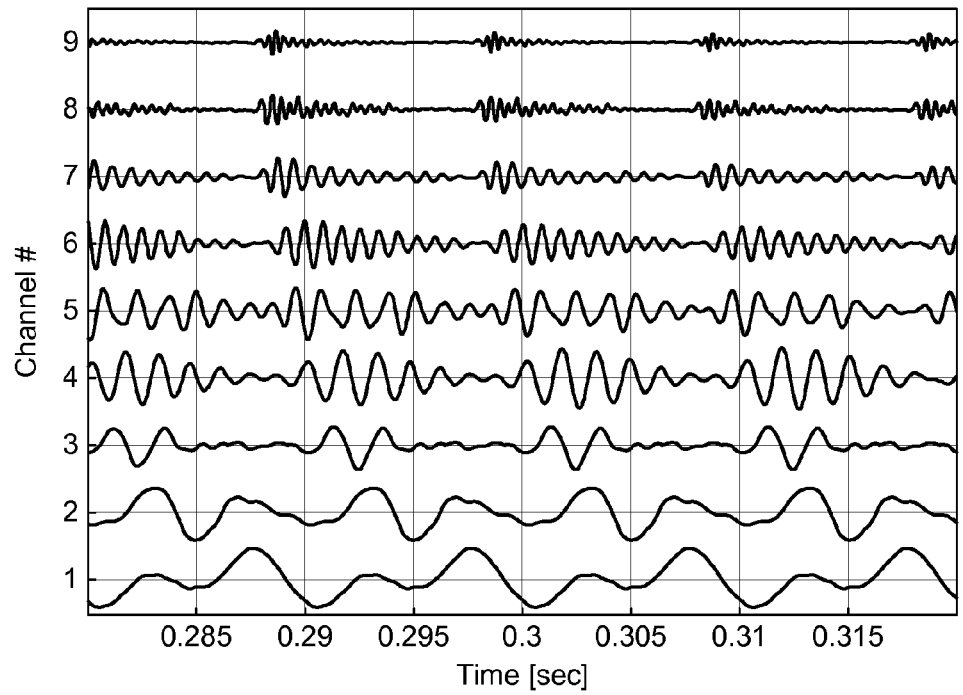
FIG. 4 shows an acoustic microphone signal decomposed by band-pass filtering by a bank of filters into a set of signals.
Figure 5:
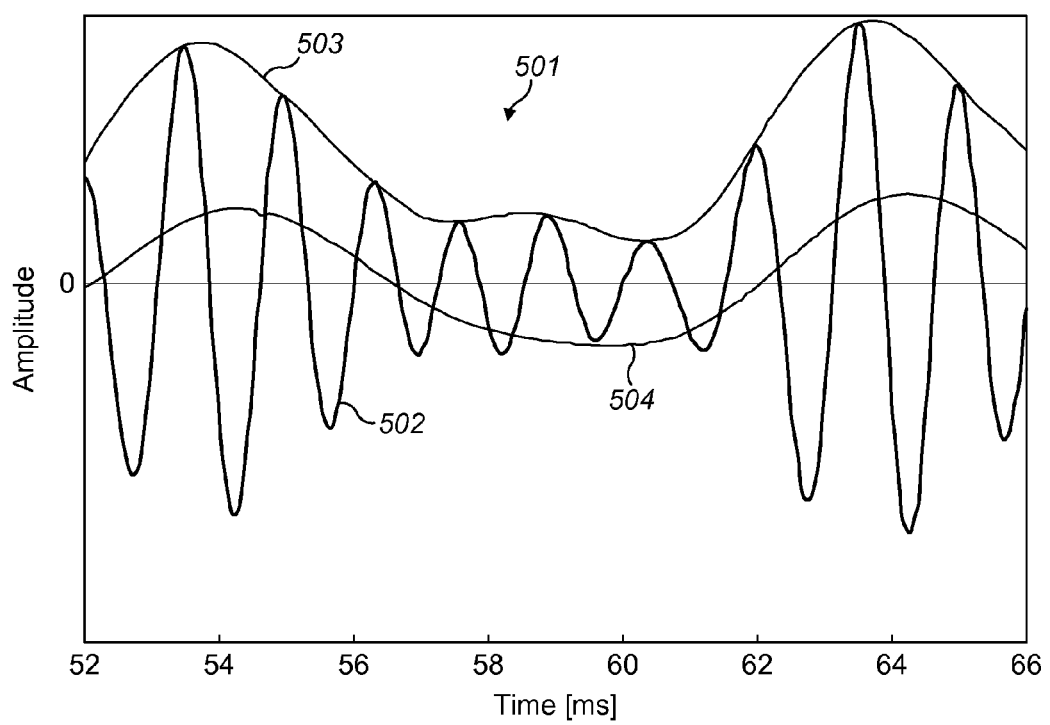
FIG. 5 a specific band pass signal and its various component parts.

Other zero crossings of the band pass fine structure component 502 trigger the non-transition stimulation pattern 702. In other different embodiments, the specific transition event that triggers a transition event stimulation pattern 701 may be some other zero crossing of the band pass fine structure component 502, the occurrence of a given multiple number of zero crossings in the band pass fine structure 502, and/or a different zero crossing of a filtered DC-free band pass envelope component 504. It is understood, that the transition event instead of a DC-free band pass envelope component 504 and zero crossing, a non-DC-free band pass envelope component 504 as shown in FIG. 5 and a threshold 504 may be used. The threshold may depend on the DC-component of the band pass envelope component 504. Similarly, this applies to the derivative of the band pass envelope signal 504.

In BPF filter bands that are broader than the fundamental frequency F0 of the input audio signal, several frequency harmonics can coincide. The F0 periods can be emphasized using different types of stimulation pulse sequences, for example, applying transition event stimulation pattern sequences at F0 periods and non-transition stimulation pattern sequences at those zero crossings of the band pass signal that do not correspond to F0 periods. The detection of F0-related band pass signal component zero crossings can be performed by using a gating technique: And the band pass envelope component signal in an affected band pass channel could be filtered with cutoff frequencies that include the frequencies of F0 modulations. Typical cutoff frequencies for an envelope filter could be 80 Hz and 300 Hz for human voices. Higher cutoff frequencies could be used to cover pitches from other non-speech sources such as musical instruments.

Using different stimulation patterns as described above can be useful to extend the frequency range of sustained neural firing as investigated by Hancock, who found that when introducing short inter-pulse intervals into the stimulation signal pulse patterns, cat inferior colliculus neurons fire in a continuous manner in response to increasing-rate pulse bursts as compared to constant rate stimuli. To extend the range of rate pitch for cochlear implant patients (the so called rate-pitch limit), stimulation signal pulse sequence patterns with short inter-phase intervals can be applied.

When applying an n-of-m signal processing scheme together with CSSS sequences, priority can be given to the CSSS sequences over other coinciding non-CSSS pulses on the signal channels that are included in the group of m band pass channels. To further extend the pitch rate limit, transition event stimulation pattern sequences with short inter-pulse sequences can be triggered based on counting zero-crossings so that the transition event stimulation pattern sequences will be applied at every integer x zero crossing of the band pass envelope signal component. The non-transition event stimulation pattern sequences can also include zero amplitude pulses.

The described methods might apply also to other specific neural stimulation systems such as vestibular prostheses. And more than two types of transition event stimulation pattern sequences could be used to code different events in the input audio signal.

Embodiments of the invention may be implemented in part in any conventional computer programming language. For example, preferred embodiments may be implemented in a procedural programming language (e.g., "C") or an object oriented programming language (e.g., "C++" or Python). Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve at least some of the advantages of the invention without departing from the true scope of the invention. For example, the approaches described herein could be applied for auditory prostheses other than cochlear implants such as an auditory brainstem implant with the electrical stimuli presented by electrodes within or adjacent to the cochlear nucleus, or an auditory midbrain implant with the electrical stimuli presented by electrodes on or within the inferior colliculus. In addition, corresponding methods and systems may also be used for deep brain stimulation.

What is claimed is:

1. An auditory implant system comprising:
    an implanted electrode array having a plurality of stimulation contacts configured for electrical stimulation of adjacent neural tissue;
    an audio input preprocessor that receives an input audio signal and generates a plurality of band pass signals, wherein each band pass signal represents an associated band of audio frequencies in the input audio signal and is characterized by band pass components including a band pass envelope and band pass fine structure;
    a band pass signal analyzer that analyzes each band pass signal to detect when one of the band pass components undergoes a defined transition event; and
    a stimulation signal generator that generates a set of electrode stimulation signals for the stimulation contacts from the band pass signals such that the electrode stimulation signals to a given stimulation contact:
        i. use a transition event stimulation pattern whenever a transition event is detected in a band pass signal associated with the given stimulation contact, and
        ii. use a different non-transition stimulation pattern after the transition event stimulation pattern until a next subsequent transition event is detected.

2. The system according to claim 1, wherein the transition event stimulation pattern forms at least one pair of sequential biphasic pulses with short inter-pulse interval.

3. The system according to claim 2, wherein the non-transition stimulation pattern forms a single biphasic pulse.

4. The system according to claim 1, wherein the transition event is onset of a voiced pitch period.

5. The system according to claim 1, wherein the transition event is a zero crossing of a filtered band pass envelope.

6. The system according to claim 1, wherein the transition event is a zero crossing of the band pass fine structure immediately following the zero crossing of a filtered band pass envelope.

7. The system according to claim 1, wherein the transition event is the occurrence of a given multiple number of zero crossings in the filtered band pass envelope.

8. A method of generating electrode stimulation signals for an implanted electrode array having a plurality of stimulation contacts, the method comprising:
    processing an input audio signal to generate a plurality of band pass signals, wherein each band pass signal represents an associated band of audio frequencies in the input audio signal and is characterized by band pass components including a band pass envelope and band pass fine structure;
    analyzing each band pass signal to detect when one of the band pass components undergoes a defined transition event; and
    generating a set of electrode stimulation signals for the stimulation contacts from the band pass signals, wherein the electrode stimulation signals to a given stimulation contact:
        i. use a transition event stimulation pattern whenever a transition event is detected in a band pass signal associated with the given stimulation contact, and
        ii. use a different non-transition stimulation pattern after the transition event stimulation pattern until a next subsequent transition event is detected.

9. The method according to claim 8, wherein the transition event stimulation pattern forms at least one pair of sequential biphasic pulses with short inter-pulse interval.

10. The method according to claim 9, wherein the non-transition stimulation pattern forms a single biphasic pulse.

11. The method according to claim 8, wherein the transition event is onset of a voiced pitch period.

12. The method according to claim 8, wherein the transition event is a zero crossing of a filtered band pass envelope.

13. The method according to claim 8, wherein the transition event is a zero crossing of the band pass fine structure immediately following the zero crossing of a filtered band pass envelope.

14. The method according to claim 8, wherein the transition event is the occurrence of a given multiple number of zero crossings in the filtered band pass envelope.

15. A computer program product implemented in a non-transitory, tangible computer readable storage medium for generating electrode stimulation signals for an implanted electrode array having a plurality of stimulation contacts, the product comprising:
    program code for processing an input audio signal to generate a plurality of band pass signals, wherein each band pass signal represents an associated band of audio frequencies in the input audio signal and is characterized by band pass components including a band pass envelope and band pass fine structure;
    program code for analyzing each band pass signal to detect when one of the band pass components undergoes a defined transition event; and
    program code for generating a set of electrode stimulation signals for the stimulation contacts from the band pass signals, wherein the electrode stimulation signals to a given stimulation contact:
        i. use a transition event stimulation pattern whenever a transition event is detected in a band pass signal associated with the given stimulation contact, and
        ii. use a different non-transition stimulation pattern after the transition event stimulation pattern until a next subsequent transition event is detected.

16. The product according to claim 15, wherein the transition event stimulation pattern forms at least one pair of sequential biphasic pulses with short inter-pulse-interval.

17. The product according to claim 16, wherein the non-transition stimulation pattern forms a single biphasic pulse.

18. The product according to claim 15, wherein the transition event is onset of a voiced pitch period.

19. The product according to claim 15, wherein the transition event is a zero crossing of a filtered band pass envelope.

20. The product according to claim 15, wherein the transition event is a zero crossing of the band pass fine structure immediately following the zero crossing of a filtered band pass envelope.

21. The product according to claim 15, wherein the transition event is the occurrence of a given multiple number of zero crossings in the filtered band pass envelope.

* * * * *